US009966580B2

(12) United States Patent
Foerger et al.

(10) Patent No.: US 9,966,580 B2
(45) Date of Patent: May 8, 2018

(54) MOUNT FOR RELEASABLY RECEIVING A DEVICE ON A MEDICAL APPARATUS, AND A CORRESPONDING MEDICAL APPARATUS

(75) Inventors: Jens Foerger, Laubuseschbach (DE); Stefan Oesterreich, Neu-Ansprach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 221 days.

(21) Appl. No.: 13/119,793

(22) PCT Filed: Sep. 18, 2009

(86) PCT No.: PCT/EP2009/006763
§ 371 (c)(1),
(2), (4) Date: May 10, 2011

(87) PCT Pub. No.: WO2010/031572
PCT Pub. Date: Mar. 25, 2010

(65) Prior Publication Data
US 2011/0210217 A1  Sep. 1, 2011

(30) Foreign Application Priority Data
Sep. 22, 2008  (DE) .................. 10 2008 048 263

(51) Int. Cl.
*H01M 2/10*  (2006.01)
*A61M 1/14*  (2006.01)

(52) U.S. Cl.
CPC .......... *H01M 2/1005* (2013.01); *H01M 2/105* (2013.01); *H01M 2/1016* (2013.01);
(Continued)

(58) Field of Classification Search
CPC .......... H02B 1/32; H02B 1/42; H01R 13/629; A61M 1/28; A61M 1/14; A61M 2206/08;
(Continued)

(56) References Cited

U.S. PATENT DOCUMENTS

| 4,429,025 A | 1/1984 | Stow |
| 4,508,794 A | 4/1985 | Wright |

(Continued)

FOREIGN PATENT DOCUMENTS

| CN | 2554800 Y | 6/2003 |
| CN | 102119017 A | 7/2011 |

(Continued)

OTHER PUBLICATIONS

"Living Hinge." Wikipedia: The Free Encyclopedia. Accessed online on Aug. 24, 2016, from http://en.wikipedia.org/wiki/Living_hinge.*

(Continued)

*Primary Examiner* — Christine H Matthews
*Assistant Examiner* — Kaylee Wilson
(74) *Attorney, Agent, or Firm* — Fish & Richardson P.C.

(57) ABSTRACT

A mount for being releasably received on a medical apparatus and for accommodating a device adapted for insertion inside the mount includes at least two side parts including a first side part and a second side part, at least the second side part or at least a portion thereof being configured so as to pass from a first position into a second position as a result of operational arrangement of the mount on the medical apparatus and/or by operational insertion of the device into the mount. In addition, a medical apparatus includes a like mount.

15 Claims, 3 Drawing Sheets

(52) U.S. Cl.
CPC ....... *H01M 2/1022* (2013.01); *H01M 2/1038* (2013.01); *H01M 2/1061* (2013.01); *H01M 2/1072* (2013.01); *H01M 2/1077* (2013.01); *A61M 1/14* (2013.01); *A61M 2205/8206* (2013.01); *A61M 2209/08* (2013.01)

(58) Field of Classification Search
CPC ............ A61M 1/3661; A61M 1/3621; H01M 2/1005; H01M 2/1077; H01M 2/1038; H01M 2/1016; H01M 2/1061; H01M 2/105; H01M 2/1072; H01M 2/1022; H01M 2205/8206
USPC ........... 128/897, 899; 248/49, 65, 67.7, 200, 248/205.1, 213.2, 223.21, 223.41–224.51, 248/224.61, 225.11, 226.11, 503, 510; 604/4.01, 6.01, 29, 261, 5.01; 210/195.2, 210/321.6–321.69, 321.71, 500.21, 646; 224/902; 446/439; 5/600, 601, 603, 611, 5/612, 613, 616; 180/68.5
See application file for complete search history.

(56) References Cited

U.S. PATENT DOCUMENTS

| | | | | |
|---|---|---|---|---|
| 4,632,201 A * | 12/1986 | Kay | ............................. | 180/68.5 |
| 5,121,806 A * | 6/1992 | Johnson | .................. | B60K 1/04 |
| | | | | 180/65.51 |
| 5,277,820 A * | 1/1994 | Ash | ............................ | 210/646 |
| 5,681,668 A * | 10/1997 | Reed | ................... | H01M 2/1072 |
| | | | | 180/68.5 |
| 5,712,482 A * | 1/1998 | Gaiser | .................. | A61B 6/4405 |
| | | | | 250/363.08 |
| 5,868,678 A | 2/1999 | Brunner et al. | | |
| 5,922,489 A | 7/1999 | Adachi | | |
| 6,050,278 A * | 4/2000 | Arnal et al. | ............... | 134/167 R |
| 6,143,181 A * | 11/2000 | Falkvall | .................. | A61M 1/16 |
| | | | | 210/143 |
| 6,181,380 B1 | 1/2001 | Toyofuku et al. | | |
| 6,230,834 B1 | 5/2001 | Van Hout et al. | | |
| 6,382,761 B1 | 5/2002 | Shinya et al. | | |
| 6,530,804 B1 | 3/2003 | Wu | | |
| 7,022,098 B2 * | 4/2006 | Wariar et al. | ................ | 604/6.08 |
| 7,035,099 B2 * | 4/2006 | Wu | ........................... | 361/679.33 |
| 2007/0090700 A1 * | 4/2007 | Matthias | ................... | B25F 5/02 |
| | | | | 310/50 |
| 2008/0038954 A1 * | 2/2008 | Gontarek et al. | ............. | 439/341 |
| 2009/0009764 A1 * | 1/2009 | Slepicka | ...................... | 356/370 |

FOREIGN PATENT DOCUMENTS

| | | |
|---|---|---|
| DE | 196 04 069 A1 | 8/1997 |
| DE | 20 2005 005 018 U1 | 8/2006 |
| DE | 20 2007 016 137 U1 | 4/2008 |
| DE | 20 2007 016137 | 4/2008 |
| EP | 0 508 248 A1 | 10/1992 |
| EP | 0 950 535 | 10/2009 |
| JP | S54-184426 U | 12/1979 |
| JP | 2001507252 | 6/2001 |
| JP | 2002 367578 | 12/2002 |
| JP | 2003 007276 | 1/2003 |
| WO | 99/36974 | 7/1999 |
| WO | 99/59841 | 11/1999 |
| WO | WO 2006/077457 | 7/2007 |
| WO | WO 2008024722 A2 * | 2/2008 ............ A61B 5/0002 |

OTHER PUBLICATIONS

PCT International Search Report for PCT/EP2009/006763 dated Dec. 28, 2009.
Japanese Search Report by Registered Searching Organization in Japanese Application No. 2011-524250, dated Aug. 9, 2013, 8 pages (with English translation).

* cited by examiner

MOUNT FOR RELEASABLY RECEIVING A DEVICE ON A MEDICAL APPARATUS, AND A CORRESPONDING MEDICAL APPARATUS

FIELD OF THE INVENTION

The present invention concerns a mount for releasably receiving both the mount and a device suited to be accommodated inside the mount. It furthermore concerns a medical apparatus.

BACKGROUND

A number of apparatus that are known from practice, in particular medical apparatus, comprise a device adapted to be releasably received, e.g., in recesses or depressions thereof. This device may be inserted or introduced into a portion of the medical apparatus and accordingly be separated again from the medical apparatus. Thus, e.g., accumulators or batteries integrated into dialysis machines are inserted in an exchangeable manner. These power sources must be replaced on a regular basis and are therefore arranged for easy insertion and removal. Exchangeability is generally also required in the case of other devices not serving for the energy supply of the medical apparatus.

It is an object of the present invention to propose another mount for releasably fastening or providing a device, in particular a power source, on an apparatus, in particular on a medical apparatus.

The object of the present invention is achieved through a mount having the exemplary features described below.

SUMMARY

Thus, in accordance with example embodiments of the present invention, a mount for being releasably received on an apparatus, in particular on a medical apparatus, is being proposed. The mount of the invention is moreover suited for receiving or accommodating therein a device in a condition of use of the mount. The mount may have an arbitrary configuration for receiving the device inside the mount or having it inserted therein. In particular, the mount is configured for receiving a device of predetermined dimensions, geometry, size, shape, or the like. In this regard, the mount and device may be adapted to each other. The mount is provided for releasably fastening the device on the medical apparatus. This condition is expressed or circumscribed by the expression "operational" as used herein.

The mount of the exemplary embodiment of the present invention comprises at least two side parts, namely, a first side part and a second side part.

At least the second side part or a portion thereof is adapted to be taken from a first position into a second position. The following explanations may unrestrictedly be transposed to further side parts in addition to the second one. Thus, the following explanations may apply, e.g., to both the first and second side parts.

The elements of the mount referred to as side parts in the context of the example embodiments of the present invention may, e.g., be configured as vertical limitations of the mount's interior. Within the framework of the present invention it is, inter alia, possible to also designate an end face as a side part.

Releasable accommodation of the mount on a medical apparatus is in particular understood to be an insertion, introduction, etc. In accordance with the example embodiments of the present invention, this process is preferably intended to take place without any tools.

Releasable accommodation of the mount on the medical apparatus preferably takes place on a portion of the casing of the medical apparatus. This preposition "on" should be understood in a broad sense. Thus, mounting on the medical apparatus may also be understood in the sense of "in the medical apparatus" or "at the medical apparatus" and the like.

The transition of the second side part or of one of its portions from the first position into the second position may, for instance, take place owing to the operational accommodation of the mount on the apparatus. This transition may thus be brought about by the step of inserting the mount on the apparatus. It may also be brought about by mere placement of the insertable device inside the mount. Depending on the respective configuration of the present invention, the transition may take place independently of whether insertion of the device in the mount and/or insertion of the mount in the medical apparatus takes place in a vertical direction, a horizontal direction, or any other direction.

In a preferred embodiment, in the first position a portion of the second side part is not in contact with a device disposed inside the mount in a condition of use of the latter. In a second position, the second side part or the portion thereof is in contact with the device.

In accordance with example embodiments of the present invention, such contact may in particular be a contiguous contact or a force-transmitting contact. Optionally it may be a frictional and/or a positive contact.

The device may be clamped in the second position—the position of contact—between the second side part and another structure of the mount such as, e.g., the first side part. The movement of the second side part from the first position into the second position or vice versa may be a movement of the second side part relative to the first side part.

In accordance with example embodiments of the present invention, a contact between the second side part and the device is not exclusively a contiguous contact between side part and device in the sense of adjacent structures actually being in touch with each other. Rather, additional elements such as spacers, insulation material, padding, and the like may furthermore be provided between side part and device. "Contact" in the context of the present invention generally is a condition wherein the side part significantly restricts the device in its movement, and in particular a condition wherein a pressure is directly or indirectly exerted on a portion of the device through the intermediary of the side part.

In a further preferred embodiment of the present invention, the mount is configured such that a distance between the first side part and the second side part or between respective portions thereof and/or a volume of the interior is reduced by operational insertion of the device in the mount from a first position into a second position.

In a further preferred embodiment of the mount of the present invention, it is proposed that the second side part passes—owing to removal of the device from the inside of the mount and/or releasing the mount from the medical apparatus—from the second position (hereinafter also referred to as "contiguous position") into the first position or into an intermediary position situated between the first position and the second position.

The transition from the second position into the first position or into the intermediary position may take place as a result of an inherent tension of the mount or of the second side part, utilization of a shape memory material, for instance by a user of the apparatus, resetting or spring means, etc.

In a further preferred embodiment according to the present invention, it is proposed that the second side part is fixedly connected to the mount in at least a portion thereof. The fixed connection may have the form of a permanent, non-releasable, or even integral connection.

The device, which the interior of the mount is configured to accommodate, may in accordance with example embodiments of the present invention be a power source for the medical apparatus. The device may therefore be configured as an accumulator or battery or the like.

The mount may in accordance with example embodiments of the present invention be configured to be integral, e.g., as a stamping or by means of a casting process or any other suitable manufacturing process, inter alia of resin or the like.

In a further preferred embodiment of the present invention, in turn, the mount comprises at least one stop for fixing a depth of reception, a penetration depth, etc., of the mount in the medical apparatus.

The mount of the present invention comprises in a further preferred embodiment at least one catch for latching the mount on a portion, in particular in an undercut, of the medical apparatus.

In a further preferred embodiment, in turn, the mount comprises at least one handle for carrying the mount, wherein the catch—where present—may be released from the latched condition on the medical apparatus, preferably by exertion of pressure on this handle.

In a further preferred embodiment, in turn, the mount of the present invention comprises at least one bottom portion for supporting the device in the mount. Through the intermediary of the bottom portion, the weight of the device may be supported by the mount.

The object of the present invention is also achieved through a medical apparatus including at least one mount of the present invention having the features described herein. This medical apparatus may preferably have the form of a dialysis apparatus. As the advantages of the present invention may be achieved equally with the mount of the present invention and with the apparatus of the present invention, reference is herewith made to their joint discussion essentially given hereinbelow.

By means of the example embodiments of the present invention it is possible to fasten a device such as an accumulator, a battery, in particular an emergency power accumulator, on a piece of medical-technical equipment, in particular on an emergency dialysis machine, with enhanced security of the retaining function. Mounting or fastening the device accommodated in the mount to the medical apparatus may be highly simplified as compared with prior-art systems. The replacement of the device may moreover advantageously imply a low expenditure of time. In accordance with example embodiments of the present invention, the placement of the device on the medical apparatus and its removal or replacement may advantageously take place without the use of tools. The mount of the present invention may advantageously be manufactured in a particularly simple and cost-efficient manner. In accordance with example embodiments of the present invention, fastening the device to the medical apparatus and releasing or replacing the device may moreover advantageously take place in a single manipulation, which in turn enhances the operating comfort and reduces the time period required.

The mount of example embodiments of the present invention is advantageously also characterized by the fact that it can safely support the weight of the device in any attitude during transport. It may furthermore have the advantage that the attitude of the device, in particular of the heavy accumulator, inside the mount while in the condition assembled on the medical apparatus may advantageously be predetermined to be invariable such as to preclude, for example, a contact of electrical terminals with conducting parts or portions, e.g., of the medical apparatus that are not intended for contact with the terminals. The present mount may be usable for devices having virtually any geometrical design.

Further features and aspects of example embodiments of the present invention are described in greater detail below with reference to the appended drawings, wherein like reference numerals designate identical or at least similar elements.

DETAILED DESCRIPTION

Figure 1:
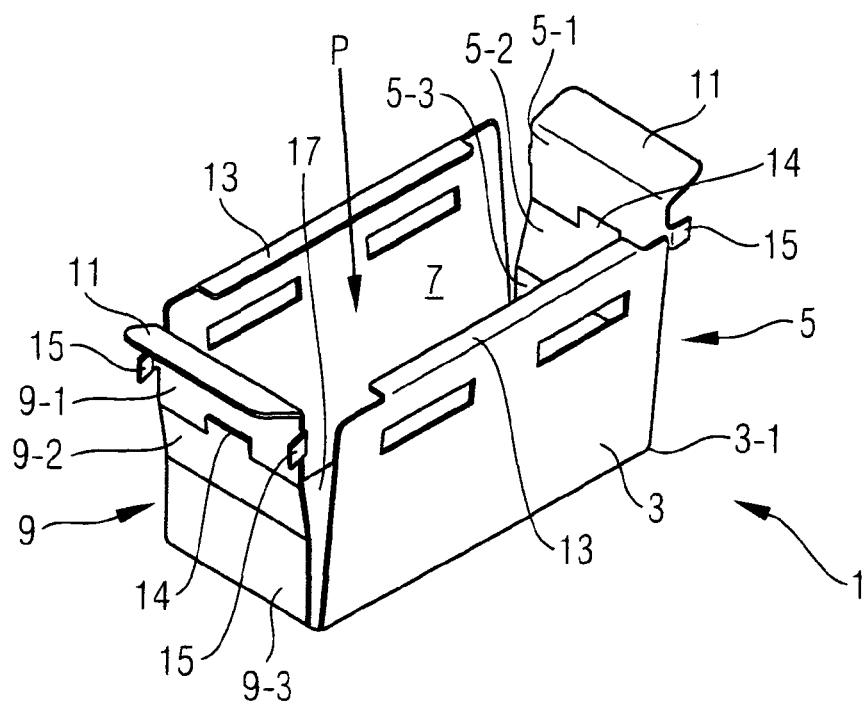
FIG. 1 shows a mount in a non-assembled condition without a device accommodated inside the mount, in accordance with example embodiments of the present invention.

FIG. 1 shows in a view obliquely from above a mount 1, in accordance with example embodiments of the present invention, having four side parts 3, 5, 7, and 9. The side parts 5, 9 include handles 11 whereby the mount 1 may easily be transported and also inserted in a medical apparatus (not represented in FIG. 1).

The side parts 3 and 7 may be configured to be adjustable between two positions so as to enlarge, by moving apart, an upper opening between two edges 13 of the side parts 3 and 7 in the non-use condition of the mount (i.e., with no battery inserted or without connection with the medical apparatus) to thus facilitate insertion, along the arrow P, of the device having the form of a battery in the example embodiment of FIG. 1.

In accordance with the representation of FIG. 1, the side parts 5 and 9 may present a slightly stepped development in a vertical direction of FIG. 1, such that upper portions 5-1 and 9-1 are further removed from each other than lower portions 5-3 and 9-3 having respective oblique portions 5-2 and 9-2 disposed between them. The stepped construction allows compression of the side parts 5 and 9 towards each other with the aid of the handles 11, such that catches 14 provided on the side parts 5 and 11 may easily and without the use of tools be disengaged from the casing (not represented in FIG. 1) of a medical device, as will be explained in further detail in the following.

The mount 1 of FIG. 1 further includes four stops 15 whereby the depth of reception or penetration of the mount 1 is limited when it is inserted vertically from above in the casing of a medical-technical apparatus (not represented in FIG. 1). The mount 1 may thus rest in the casing of the medical apparatus while being supported by the stops 15.

In the assembled condition of the mount 1, the side parts 3 and 7 approach each other at least in their upper ranges. When the mount 1 is again removed from the medical-technical apparatus, they again recede from each other. The mount may, however, also be configured such that the side parts 3 and 7 move apart in portions thereof as a result of removing the battery (not represented in FIG. 1).

In accordance with the representation in FIG. 1, the mount of the example embodiment of the present invention represented therein includes a bottom portion 17 to which the side parts 3, 5, 7, and 9 connect. According to example embodiments of the present invention it is, however, also possible to configure the mount 1 without such a bottom portion 17. In such example embodiments, retaining or supporting portions for carrying the device to be inserted inside the mount 1 are provided, e.g., on the side walls in alternative to the bottom portion 17.

Figure 2:
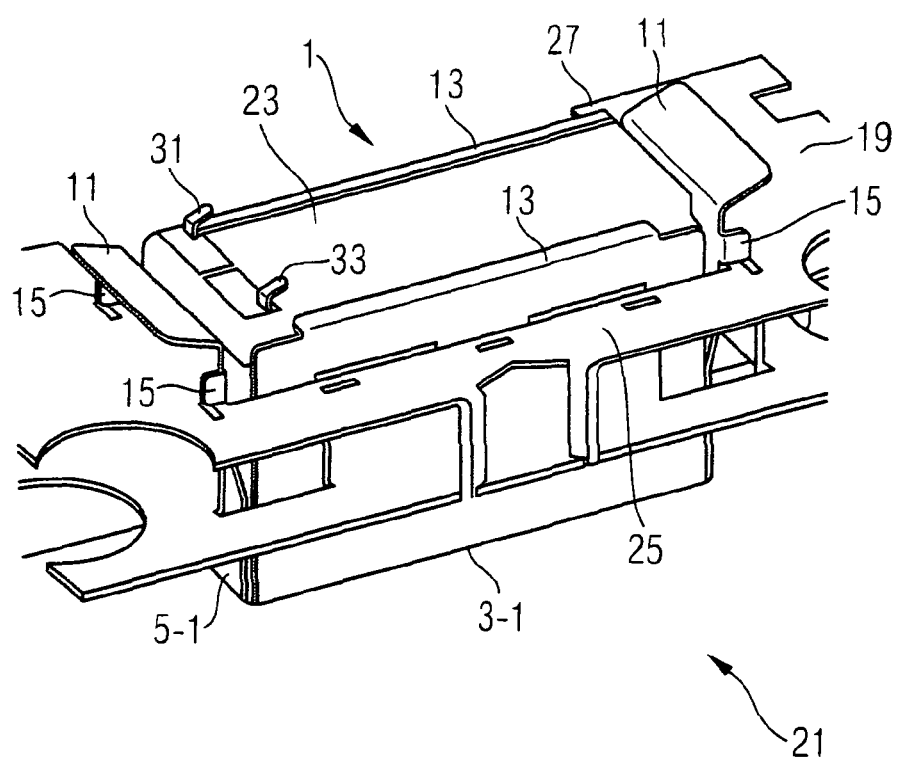
FIG. 2 shows the mount of FIG. 1 with a battery accommodated therein in the assembled condition in a medical apparatus when viewed obliquely from above.

FIG. 2 shows the mount 1 of the example embodiment of the present invention according to FIG. 1 in the assembled condition in a casing 19 of a medical apparatus 21. In the representation of FIG. 2, the mount 1 comprises inside it a device 23 having the form of a battery including terminals 25 and 27.

In FIG. 2 it can be seen how the mount 1 is supported on an upper range of the casing 19 of the medical apparatus 21 by the stops 15 and how these accordingly determine the extent to which the mount 1 inserted vertically from above into the medical apparatus 21 enters or penetrates into the latter.

In FIG. 2 it can be seen how the limitation of the opening width for the mount 1 in the casing 19 due to casing portions 25 and 27 in the event of its insertion causes the side parts 3, 5 to approach each other such that the portions or edges 13 encompass the device 23 from above or clamp it laterally to thus restrict a movement thereof and thus fasten or secure it.

An enclosed condition of the upper range of the battery having terminals 31 and 33 or of the device 23, i.e. in the area of its electrical contact, therefore exists.

In the embodiment of FIGS. 1 and 2, the side part 3 is integrally connected to the bottom portion 17 in a lower portion 3-1 thereof having the form, for instance, of a fold. The same may also be true for the side parts 5, 7, and 9.

Figure 3:
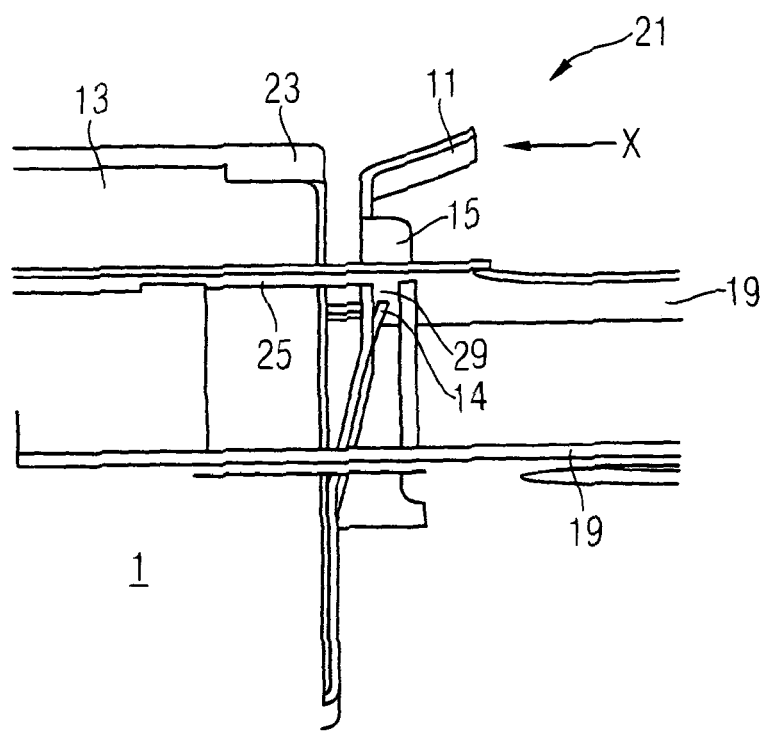
FIG. 3 is a partial view of a mount inserted in a medical apparatus, in accordance with example embodiments of the present invention.

FIG. 3 is a partial, slightly tilted lateral view of a mount 1 of the example embodiment of the present invention while arranged in the casing 19 of the apparatus 21. In FIG. 3, the catch 14 of the mount 1 of the present invention is visible, which—owing to an inherent tension of the side part 5 carrying the catch 14—engages a portion 29 of the casing 19 such as to prevent a release of the mount 1 from the casing 19 of the medical apparatus 21 in an upward direction, i.e., in a vertical direction. By pressing the handle 11 in the direction designated by the arrow X, it is possible to release or unlock the catch 14 from portion 29 of the casing 19 in order to remove the mount 1 from the medical apparatus 21.

The invention claimed is:

1. A medical apparatus comprising:
a casing defining an opening; and
a mount that is releasably coupleable with the casing, wherein portions of the mount reside on each side of the opening while the mount is coupled with the casing, the mount comprising:
  a bottom portion;
  multiple side parts directly connected to and extending from the bottom portion, the multiple side parts cooperating with the bottom portion to define a space to contain a device; and
  multiple stop members extending from the multiple side parts such that, while the mount is coupled with the casing, the multiple stop members rest in contact with the casing to support the mount on the casing,
wherein the mount further comprises a first catch mechanism and a second catch mechanism that are each engageable with the casing to releasably lock the mount to the casing while the mount is coupled with the casing, wherein the first catch mechanism is attached to a first one of the multiple side parts, and wherein the second catch mechanism is attached to a second one of the multiple side parts positioned on an opposing end of the bottom portion in comparison to the first one of the multiple side parts, and
wherein the mount is constructed such that a compression of both: (i) the first one of the multiple side parts and (ii) the second one of the multiple side parts towards each other disengages the first catch mechanism and the second catch mechanism from being locked to the casing.

2. The medical apparatus of claim 1, wherein the multiple stop members establish a depth of reception of the mount in the casing while the mount is coupled with the casing.

3. The medical apparatus of claim 2, wherein while the mount is coupled with the casing the multiple stop members and the catch mechanisms are on opposite sides of the opening.

4. The medical apparatus of claim 1, further comprising the device, and wherein the device comprises a power source for the medical apparatus.

5. The medical apparatus according to claim 1, wherein the medical apparatus is a dialysis apparatus.

6. The medical apparatus of claim 1, wherein the space is volumetrically larger while the mount is separated from the casing as compared to while the mount is coupled with the casing.

7. The medical apparatus of claim 6, wherein the two opposing side parts of the multiple side parts are spaced farther apart from each other while the mount is separated from the casing than while the mount is coupled with the casing.

8. The medical apparatus of claim 7, wherein the casing presses the two opposing side parts of the multiple side parts toward each other while the mount is coupled with the casing.

9. The medical apparatus of claim 8, wherein, while the mount is coupled with the casing, the casing presses the two opposing side parts of the multiple side parts toward each other to releasably capture the device within the space.

10. The medical apparatus of claim 1, wherein the compression of both: (i) the first one of the multiple side parts and (ii) the second one of the multiple side parts comprises a concurrent pressing towards each other of the first one of the multiple side parts and the second one of the multiple side parts.

11. The medical apparatus of claim 1, wherein the multiple side parts comprise four side parts, and wherein none of the four side parts are directly attached to each other.

12. The medical apparatus of claim 11, wherein the bottom portion is quadrilateral, and wherein each of the four side parts is directly attached to a respective side of the quadrilateral.

13. The medical apparatus of claim 1, wherein the mount is unlockable from the casing by a manual manipulation of a respective one of the two opposing side parts to which the first catch mechanism and the second catch mechanism is attached.

14. The medical apparatus of claim 1, wherein the casing defines a recess in which the mount is releasably coupleable.

15. The medical apparatus of claim 1, wherein the mount has an integral configuration such that the multiple side parts are integrally connected to the bottom portion.

* * * * *

UNITED STATES PATENT AND TRADEMARK OFFICE
CERTIFICATE OF CORRECTION

PATENT NO. : 9,966,580 B2  
APPLICATION NO. : 13/119793  
DATED : May 8, 2018  
INVENTOR(S) : Jens Foerger and Stefan Oesterreich Page 1 of 1

It is certified that error appears in the above-identified patent and that said Letters Patent is hereby corrected as shown below:

On the Title Page

Item (75) Inventors, Line 2, delete "Neu-Ansprach" and insert --Neu-Anspach--.

Signed and Sealed this
Third Day of July, 2018

Andrei Iancu
*Director of the United States Patent and Trademark Office*